United States Patent [19]

Plum

[11] Patent Number: 5,298,224
[45] Date of Patent: Mar. 29, 1994

[54] APPARATUS FOR DETERMINATION OF THE COAGULATION TIME OF A BLOOD SAMPLE

[75] Inventor: Thomas M. Plum, Skodsborg, Denmark

[73] Assignee: Novo Nordisk A/S, Bagsvaerd, Denmark

[21] Appl. No.: 957,643
[22] PCT Filed: Dec. 29, 1988
[86] PCT No.: PCT/DK88/00224
§ 371 Date: Sep. 5, 1990
§ 102(e) Date: Sep. 5, 1990
[87] PCT Pub. No.: WO89/06803
PCT Pub. Date: Jul. 27, 1989

Related U.S. Application Data

[63] Continuation of Ser. No. 536,571, Sep. 5, 1990, abandoned.

[30] Foreign Application Priority Data

Jan. 14, 1988 [DK] Denmark .................................. 157/88

[51] Int. Cl.⁵ ...................... G01N 21/00; G01N 33/48
[52] U.S. Cl. .................................. 422/73; 422/82.05; 422/82.07; 356/39; 356/440; 73/64.43; 128/DIG. 22
[58] Field of Search .................. 422/73, 82.05, 82.07; 436/69; 73/64.1; 128/637, DIG. 22; 356/39, 440

[56] References Cited

U.S. PATENT DOCUMENTS

| | | | |
|---|---|---|---|
| 3,158,445 | 11/1964 | Huff | 73/64.1 X |
| 3,527,542 | 9/1970 | Penhasi et al. | 356/39 |
| 3,734,622 | 5/1973 | Adler | 356/338 |
| 3,905,769 | 9/1975 | Carroll et al. | 436/69 |
| 4,105,411 | 8/1978 | Biver | 73/64.1 X |
| 4,156,570 | 5/1979 | Wardlaw | 356/39 X |
| 4,163,615 | 8/1979 | Kwasman | 356/39 |
| 4,210,026 | 7/1980 | Amos et al. | 73/425.6 |
| 4,212,204 | 7/1980 | St. Amand | 73/425.6 |
| 4,227,815 | 10/1980 | Hoffa | 356/436 |
| 4,589,774 | 5/1986 | Dupree et al. | 356/440 X |
| 4,685,059 | 8/1987 | Yamamoto | 422/82.05 X |
| 4,876,069 | 10/1989 | Joshimsen | 422/73 |
| 4,949,400 | 8/1990 | Leveen et al. | 356/440 X |

FOREIGN PATENT DOCUMENTS

| | | |
|---|---|---|
| 786553 | 6/1968 | Canada ........................ 73/55 |
| 0120715 | 10/1984 | European Pat. Off. . |
| 1324004 | 2/1990 | U.S.S.R. . |

OTHER PUBLICATIONS

Vurek et al., Wiley Biomedical Publication, Microtechniques for the Clinical Laboratory, ch. 4, pp. 55–64 (1976).

*Primary Examiner*—Robert J. Warden
*Assistant Examiner*—T. A. Trembley
*Attorney, Agent, or Firm*—Steve T. Zelson

[57] ABSTRACT

With a blood measuring apparatus according to the invention, which uses capillary tubes (16, 17), these can be filled with blood from a drop of blood of about 1 microliter. This small amount of blood can be produced by the pricking of a finger. The blood sample can then be placed in an apparatus (1) with equipment for the determination of the blood by transillumination. The tubes (16, 17) are mounted in an independent plate piece (6), and the tubes are secured in V-form so that the inlet ends lie closely up against each other. This provides the possibility of filling two tubes at the same time, and herewith the possibility of simultaneous determination of one's own blood and a comparison with blood in, for example, a prepared tube.

5 Claims, 3 Drawing Sheets

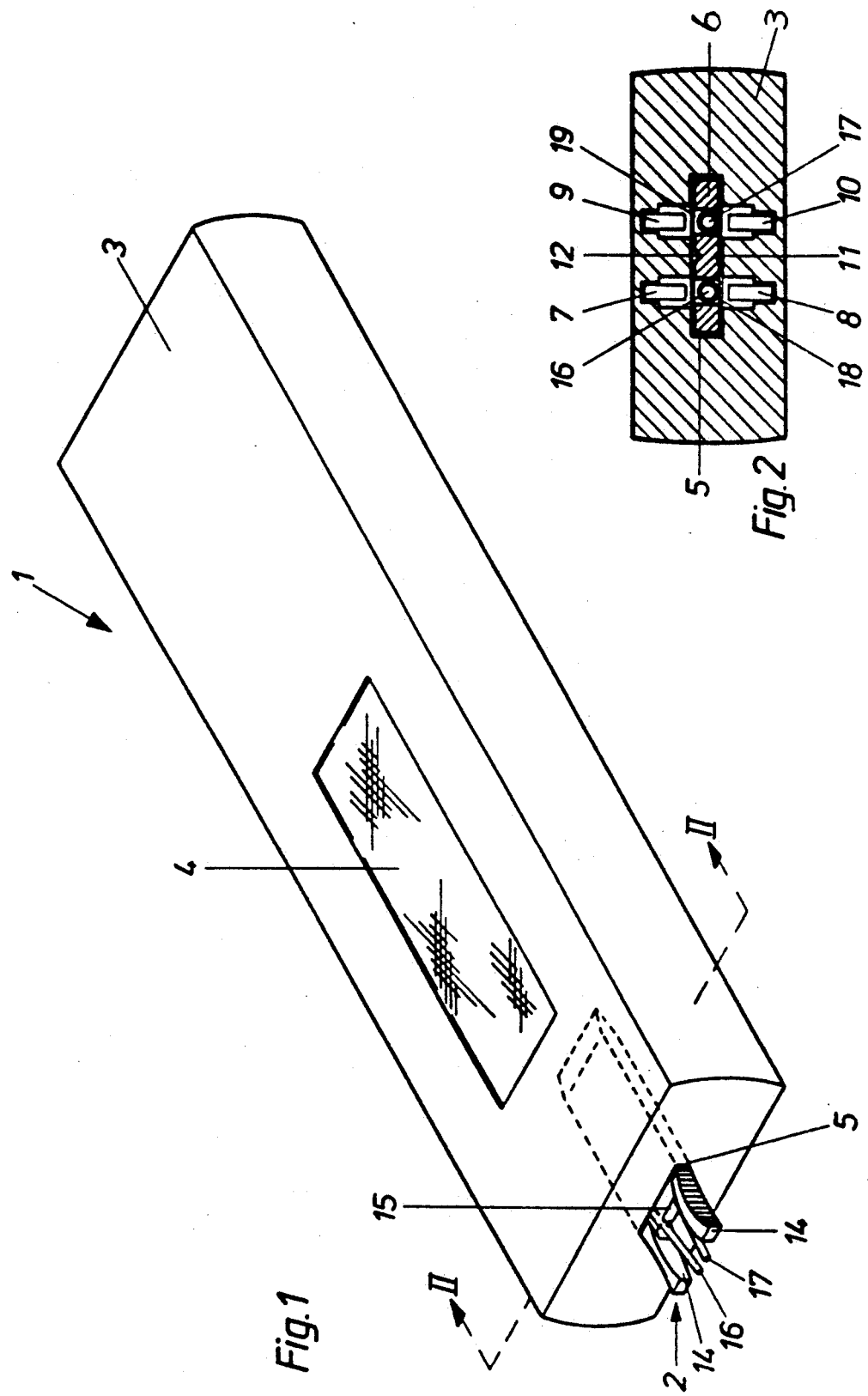

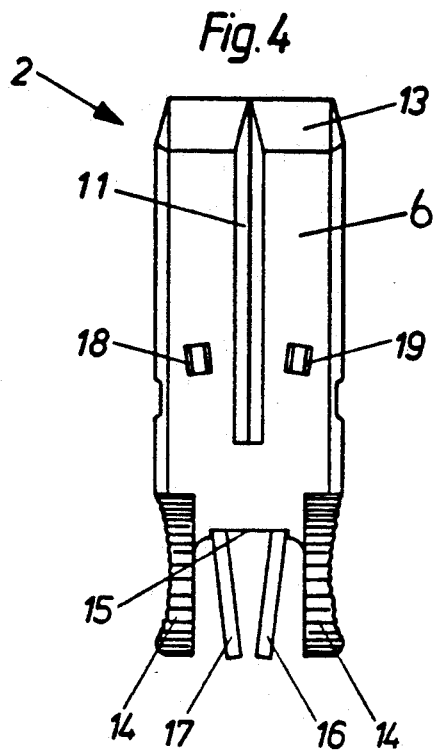
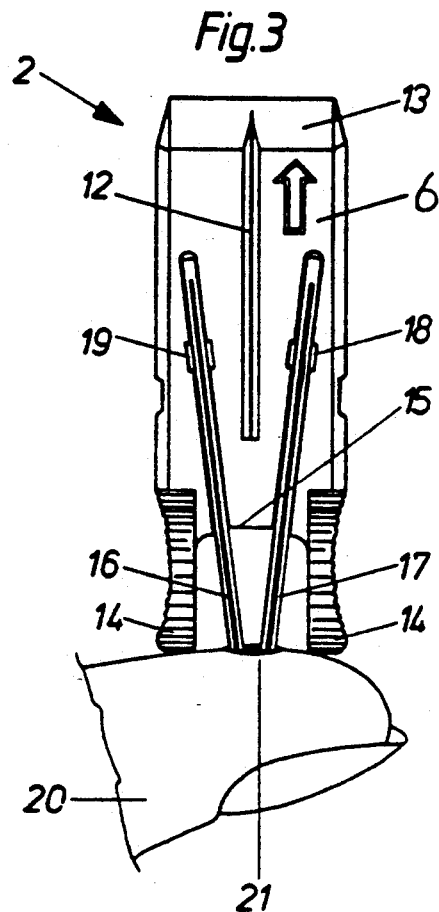
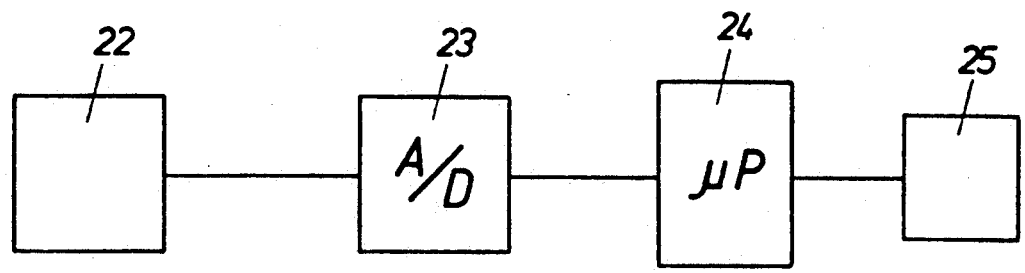

10

APPARATUS FOR DETERMINATION OF THE COAGULATION TIME OF A BLOOD SAMPLE

This application is a continuation application of co-pending application Ser. No. 07/536,571 filed Sep. 5, 1990, now abandoned.

FIELD OF THE INVENTION

The invention relates to an apparatus for the measuring of a blood sample, and comprising transparent capillary elements for taking up the blood, and a housing-mounted photometer with measuring cells for the optical detection of the light permeability of the sample in the capillary element, and which is connected to a computer for the determination of the coagulation time of the sample.

BACKGROUND OF THE INVENTION

Apparatus of this kind is used particularly by haemophilia patients for measuring the coagulability of the blood, and hereby for the determination of whether there is need for the injection of a factor VIII preparation in order to avoid haemorrhages.

Equipment of this kind is known from EP publication no. 120 715. Here, the capillary element consists of a measuring cell in the form of an elongated channel at the end of a holder. Blood is sucked up into the channel, and the measuring cell can hereafter be inserted into a measuring apparatus with a light source and a photometer. The photometer measures the amount of light which, after the emission, passes the transparent side of the measuring cell, and which after reflection in the blood and the back of the measuring cell again passes through the transparent side.

This measuring cell does not, however, provide an accurate measurement result, the reason being that it is based on reflection. This gives rise to a measurement inaccuracy which is so great that it is unsuitable for the measurement of the coagulability of the blood. Furthermore, it is difficult to produce such a measuring cell, the reason being that the capillary element is built up of at least two parts which must be assembled for the formation of an element.

From the Swedish publication no. 404 260, an apparatus is known which can measure with greater accuracy, since this uses a beam of light and light detecting elements which are placed at an angle in relation to the light's direction of incidence in the sample.

However, this apparatus demands a precisely balanced positioning of these measuring means in relation to the blood sample, and in practice this means that the blood must be kept in a vessel-like container during the measurement. Since at a minimum there must be sufficient blood to cover the light detectors, a considerable amount of blood is required. This is a serious drawback for the user, the reason being that such a large amount of blood in practice can be obtained only with the help of a suction pump and hypodermic. Therefore, this apparatus is not suitable for so-called home use, where the user himself must be able to remove the blood sample necessary for a measurement.

SUMMARY OF THE INVENTION

It is the object of the invention to remedy these deficiencies and disadvantages of the known kinds of apparatus, and this is achieved by means of an apparatus where each capillary element constitutes a glass or a plastic tube, the inside diameter of which is less than 0.5 mm.

The accuracy of measurement achieved hereby is considerably increased, since one can transilluminate the blood in the tube transversely to said tube. This reduces the measurement inaccuracy, the reason being that the tube can be produced with precise dimensions and of a homogenous material. This makes it well-suited for use in the measurement of the coagulability of the blood.

Furthermore, for reasons of the small internal diameter of the tube, a considerably smaller amount of blood is required in relation to the known types of measuring apparatus. For the filling of a tube length of, for example, 30 mm, less than 1 microliter liter is required. In practice, a drop of blood procured by, for example, the pricking of a finger, could fill several tubes, which provides the possibility of filling, for example, a prepared and an unprepared tube from one and the same drop of blood.

The apparatus thus becomes convenient to use, in that it is simple and quick to remove and take up a drop of blood in the tubes for use in the measurement.

By mounting the tubes on an independent support element, e.g. in the form of a plate piece, the sample can easily be handled and filled, after which it can be placed in the measuring apparatus.

By providing openings in the support piece opposite the tubes, the passage of light through the blood will easily be ensured by placing light sources and detectors on each side of the opening in the apparatus.

By allowing the one end of the tubes to extend some distance outside the plate piece itself, it will be a simple matter to place the tube ends in the drop of blood.

By allowing the tube ends to lie closely up against each other, one will be able to fill several tubes from a single drop of blood.

By allowing the tubes to be placed in a fan-shaped manner, it will be possible to transilluminate several tubes at a time in the apparatus, without any danger of the measurements being mutually influenced.

By providing the support piece with an extension on each side around the tube ends, one will be able to hold the element between two fingers, and also to use the extensions as support, for example against the skin of the finger, during the taking up of the blood.

Finally, it is expedient, to be able to insert the element directly into a slot in the measuring apparatus, in that the positioning of the tube in relation to the photo element will then always be ensured.

BRIEF DESCRIPTION OF THE DRAWINGS

The invention will now be described in closer detail with reference to the drawing, where FIG. 1 shows a perspective illustration of an apparatus with support element inserted, FIG. 2 shows a cross-sectional drawing of the apparatus seen in the direction II—II in FIG. 1, FIG. 3 shows the support element seen from the side during the filling of the tubes from a finger, FIG. 4 shows the support element seen from the opposite side, FIG. 5 shows a block diagram of the measuring equipment in the apparatus.

DESCRIPTION OF THE PREFERRED EMBODIMENT

Figure 6:
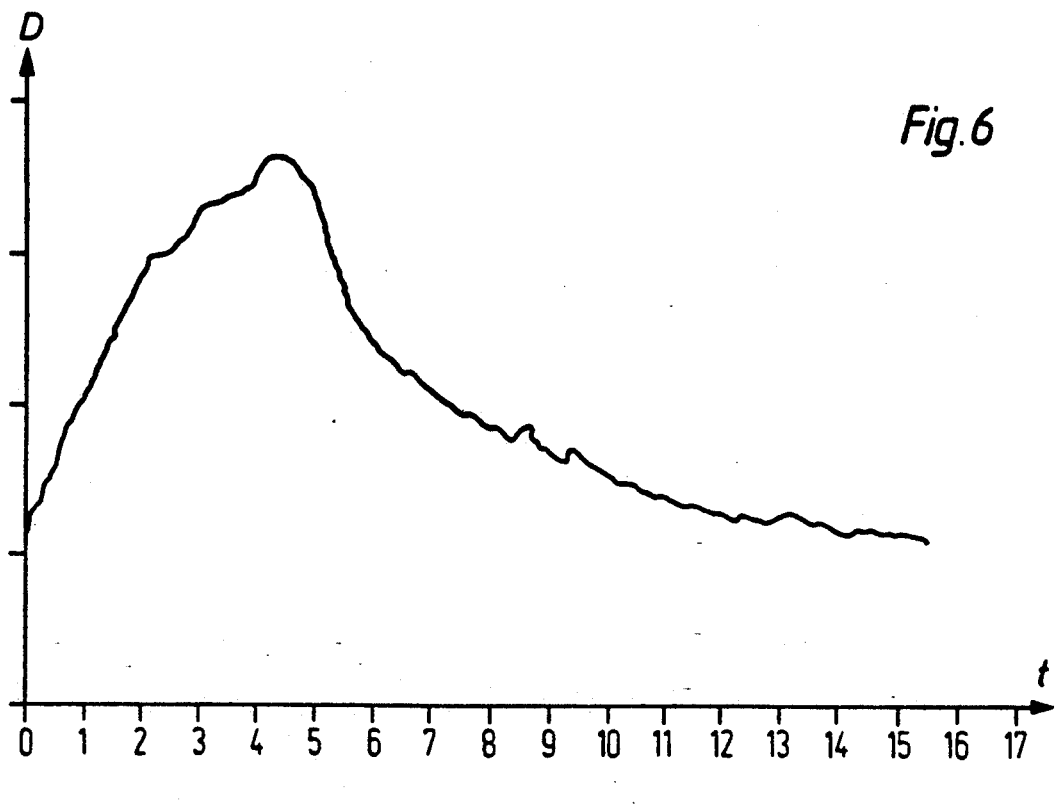
FIG. 6 shows a graph of the translucency D in normal blood as a function of the time t.

In FIG. 1 is shown an example of a preferred embodiment of an apparatus according to the invention.

The measuring apparatus itself is indicated as a whole by the reference FIG. 1. It comprises a housing 3 with a display 4 on the one side.

At the one end of the housing 3 there is provided a slot opening 5 in which a support element with capillary tubes, which is shown as a whole by the reference FIG. 2, can be inserted, as shown in FIG. 1.

As shown in FIG. 2, one or more light sources 7, 9, preferably in the form of light diodes, are mounted in the one part of the housing 3 in relation to the slot opening 5, plus a light meter, preferably in the form of a photodiode 8, 10, is mounted in the other part of the housing in relation to the slot opening.

The apparatus is also provided with a built-in but not shown microprocessor, which is connected as illustrated in the block diagram shown in FIG. 5.

In this diagram, the apparatus itself is indicated by the block 22, which is connected to an analog/digital converter 23 which converts the signal from the photodiodes 8, 10 to a figure which is read into a microprocessor 24. This is arranged to analyse the signal from the measurement and to supply pulses to a display 25 on the apparatus, which in FIG. 1 is indicated by the reference FIG. 4.

Figure 7:
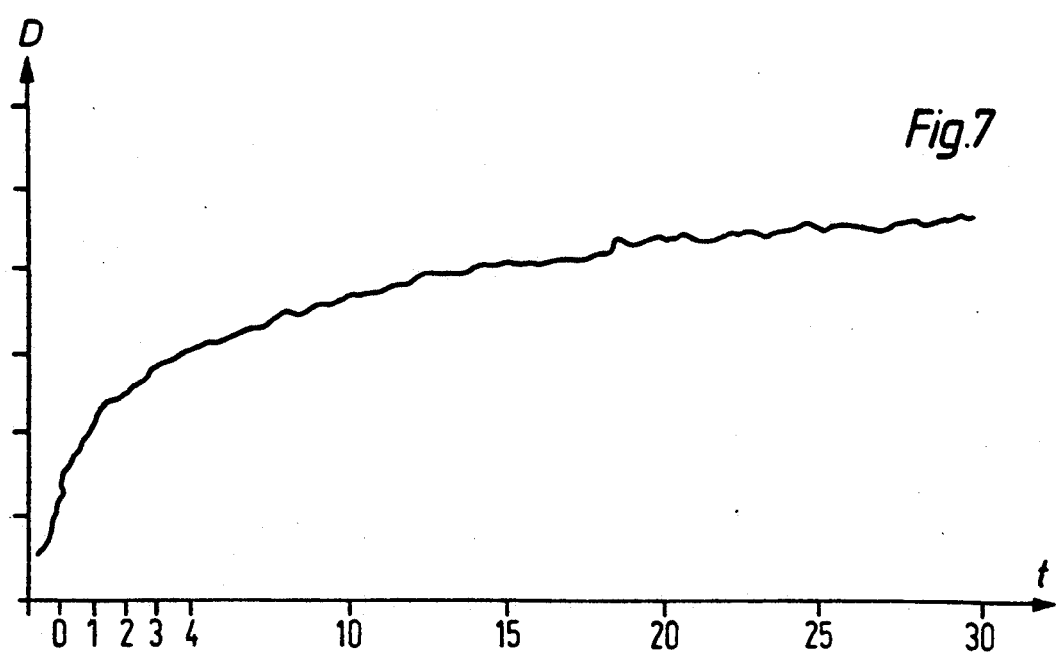
FIG. 7 shows a corresponding graph for the blood of a haemophilia patient.

By depicting the signal from this photometer as a function of time, a diagram as shown in FIGS. 6 and 7 is obtained.

Blood with a normal coagulation characteristic will, after a period of time, in the example in FIG. 6 after approx. 5 mins., show a markedly decreasing light permeability for reasons of the coagulation of the blood.

As shown in FIG. 7, such a marked decrease does not appear with blood from a haemophilia patient.

Therefore, the blood's permeability to light can be used for the determination of the coagulation time, and hereby for indication of the need for an injection of a factor VIII preparation.

When a blood sample is thus placed in a capillary element between the light sources 7, 9 and the photodiodes 8, 10 in an apparatus 1, from the display 4 one will be able to read the period of time which it takes for the blood to begin to coagulate, and which corresponds to the turning point in the graph shown in FIG. 6.

As shown in FIGS. 3 and 4, the capillary element according to the invention comprises a support piece 6, which is preferably made of an opaque plastic. This is in the form of a plate which, as shown at its one end, is tapered to form a wedge 13 for easy insertion into the slot 5 in the apparatus.

At the opposite end of the plate piece, a pair of extensions are provided in the form of legs 14, the outer sides of which are slightly concave and provided with small serrations for easy handling during operation.

Moreover, the top and bottom sides of the plate piece are provided with a pair of grooves or guide tracks 11, 12 to ease the guiding of the plate during insertion into the apparatus.

Finally, on the one side there are formed two recesses which extend at a mutual angle, and in which a glass or plastic capillary tube 16, 17 can be secured, for example by gluing. Moreover, at a suitable place in each recess there is a through-going opening 18, 19.

When the support element 2 is inserted in the apparatus, the openings 18, 19 must be placed precisely opposite the light diodes and the photodiodes as shown in FIG. 2.

As shown in FIGS. 3 and 4, the capillary tubes 16, 17 project for a distance beyond the plate edge 15, and also a small distance beyond the ends of the legs 14.

Glass is well-suited for the tube, the reason being that its electro-negative characteristics ensure a uniform starting time for the coagulation of the blood. Furthermore, an internal diameter of about 0.2 mm will be sufficient to ensure that the result of the measurement is reliable. If the glass has a length of approx. 30 mm, its capacity will be about 1 microliter. It is of great importance that more blood is not demanded, in that one can hereby carry out a blood test on the basis of a single drop of blood.

As shown in FIG. 3, the blood sample can be taken from a drop 21 on a finger 20, which is first pricked e.g. by means of a not-shown lancet. When the drop of blood has been formed, the support element 2, held by means of two fingers against the legs 14, is brought to bear against the finger so that the ends of the tubes 16, 17 are dipped in the blood. Hereafter, blood is taken up into the tubes 16, 17 in such an amount that it fills out the tubes opposite the openings 18, 19.

The support element 2 is then conveyed to the measuring apparatus, where it is inserted in the opening 5.

After the insertion, the measuring procedure commences and, after a short period of time, the measuring apparatus registers the time at which the coagulation starts, and shows this time on the display 4. In this simple manner, the patients themselves can measure their blood and decide whether there is need for an injection.

Where the user has difficulty in handling the relatively small support element 2, it can be of advantage to insert the element into the measuring apparatus before taking the blood sample, and thereafter apply the apparatus and therewith the support element with the tubes down on the drop of blood. In this way, one can more easily handle and control the support element while taking the blood sample.

After the measurement, the support element with the blood sample can be removed and discarded, in that the support element is a disposable product to simplify the operation and at the same time ensure the greatest possible hygiene.

One of the tubes 16, 17 can be provided with an internal coating of a material, e.g. a factor VIII preparation, the concentration of which is desired to be measured in the blood and compared with that blood which has been taken up into the second tube. This second tube is not provided with an internal coating, and is therefore a dry tube which will contain the patient's own blood. A patient can hereby simultaneously determine his blood's factor VIII concentration.

In the foregoing, the displaying of the result of the measurement has been discussed only in the form of a time-related indication, but it lies within the scope of the invention to use other corresponding parameters for the determination of factors which are of importance for the result of the analysis.

I claim:

1. Apparatus for the measuring of a blood sample comprising:

a support plate piece having mounted thereon and secured thereto transparent glass or plastic capillary tubes for the taking up of a blood sample from a user, said support plate piece being formed so as to enable insertion into an opening on a separate housing means;

said support plate piece further being formed with an opening adjacent each capillary tube, with each opening being aligned substantially perpendicular to the axis of said capillary tubes piece so as to allow the passage of light through the support plate piece and said transparent capillary tube and a separate housing means comprising a light source and light detector for each of said transparent capillary tubes, said light source and light detector being used to determine the light permeability of a blood sample in said transparent capillary tube, said light source being mounted opposite said light detector being mounted within said separate housing means so as to be aligned on opposite sides of said openings on said support plate piece upon the insertion of said support plate piece into an opening formed on said separate housing means, said light source and light detector further being connected to a computer whereby said computer calculates said blood sample's coagulation time based on the light permeability of said blood sample in said capillary tubes.

2. Apparatus according to claim 1, wherein one end of each of said capillary tubes (16, 17) extends for a distance beyond the edge (15) portion of the of the support plate piece (6) which is inserted into said separate housing means.

3. Apparatus according to claim 2, wherein the ends of said capillary tubes which extend beyond said support plate piece lie closely up against each other.

4. Apparatus according to claim 3, wherein the ends of said capillary tubes which are mounted in the portion of said support plate piece are further apart then the ends of said capillary tubes which extend beyond the edge portion of said support plate piece.

5. Apparatus according to claim 4, wherein said support plate piece (6) is provided with a pair of fingergrips (14) which extend from the edge (15) portion of the support plate piece (6) which is to be inserted into said separate housing means and wherein said capillary tubes (16, 17) are disposed between said fingergrips whereby said support plate piece (6) may be held by said fingergrips to obtain a blood sample and to be inserted into said separate housing means.

* * * * *